(12) United States Patent
Valdez et al.

(10) Patent No.: US 6,825,227 B2
(45) Date of Patent: Nov. 30, 2004

(54) METHOD FOR FIGHTING AGAINST ARTHROPODS DESTRUCTIVE OF CROPS AND COMPOSITIONS THEREFOR

(75) Inventors: Léopoldo Valdez, Laguna (PH); Paul Tolentino, Muntinlupa (PH); David Lobo, Laguna (PH); Arlin Bostian, Craponne (FR); Richard Dickmann, Beijing (CN)

(73) Assignee: Bayer CropScience S.A., Lyons (FR)

( * ) Notice: Subject to any disclaimer, the term of this patent is extended or adjusted under 35 U.S.C. 154(b) by 0 days.

(21) Appl. No.: 10/220,820

(22) PCT Filed: Mar. 8, 2001

(86) PCT No.: PCT/FR01/00696

§ 371 (c)(1),
(2), (4) Date: Mar. 13, 2003

(87) PCT Pub. No.: WO01/65941

PCT Pub. Date: Sep. 13, 2001

(65) Prior Publication Data

US 2003/0187029 A1 Oct. 2, 2003

(30) Foreign Application Priority Data

Mar. 8, 2000 (FR) .............................. 00 02957

(51) Int. Cl.$^7$ .......................... A01N 43/56; A01N 53/00
(52) U.S. Cl. ....................... 514/407; 574/521; 574/531; 424/405; 424/406
(58) Field of Search ................................ 424/405, 406; 514/531, 407, 521

(56) References Cited

U.S. PATENT DOCUMENTS 5,516,787 A    5/1996    Takada

FOREIGN PATENT DOCUMENTS

| EP | 0295117 A1 | | 12/1988 |
| EP | 0460940 A1 | | 12/1991 |
| EP | 0484165 A1 | | 5/1992 |
| JP | 11-49618 | * | 2/1999 |
| WO | 95/22902 A1 | | 8/1995 |
| WO | 96/16543 A2 A3 | | 6/1996 |
| WO | 98/28279 A1 | | 7/1998 |

OTHER PUBLICATIONS

*Chem. Abstracts*, vol. 130, No. 17 (Apr. 26, 1999), published by the American Chemical Society, Columbus, Ohio, XP 002154072, abstract of JP 11049618, published Feb. 23, 1999.

*The Pesticide Manual*, ed. C.D.S. Tomlin, 11$^{th}$ edition, entry Nos. 70, 176 179, 183, 184, 185, 186, 187, 204, 312, 319, 337, 333, 362, 561, 564, 687, and 718, (1997), published by The British Crop Protection Council, Farnham, Surrey, UK.

* cited by examiner

Primary Examiner—Neil S. Levy
(74) Attorney, Agent, or Firm—Hutchison & Mason PLLC

(57) ABSTRACT

The present invention relates to processes for controlling arthropods, particularly processes for controlling insects and especially processes for controlling insects which ravage crops, particularly rice crops or market-garden crops; as well as to processes for protecting crops, particularly rice crops or market-garden crops; as well as to processes directed towards improving the yield of the treated crops; as well as to compositions or products which may be used in such processes.

11 Claims, No Drawings

METHOD FOR FIGHTING AGAINST ARTHROPODS DESTRUCTIVE OF CROPS AND COMPOSITIONS THEREFOR

DESCRIPTION

The present invention relates to processes for controlling arthropods, particularly processes for controlling insects and especially processes for controlling insects which ravage crops, particularly rice crops or market-garden crops; as well as to processes for protecting crops, particularly rice crops; as well as to processes directed towards improving the yield of the treated crops; as well as to compositions or products which may be used in such processes.

More specifically, the present invention relates to processes as mentioned above which use specific insecticidal compounds in combination with other insecticidal compounds that are also specific; these are usually processes combining, in a particularly advantageous manner, the action of an insecticidal compound (A) comprising a pyrazole group and the action of an insecticidal compound (B), particularly an insecticidal compound of the pyrethroid family.

The literature discloses processes using a wide variety of insecticidal compounds. However, the known insecticidal compounds used in such processes, although having certain insecticidal effects, often do not make it possible to overcome numerous problems encountered by the users of such products, in particular users seeking specific solutions tailored to quite specific uses.

International patent application WO 95/22902 is known, which discloses certain insecticidal processes that are useful for controlling termites and which use certain specific compounds of the fiprole family with pyrethroids.

Processes for controlling certain specific types of chrysomeles which attack corn crops, and which use a specific pyrazole with certain compounds of the pyrethroid family, are also known from American patent application Ser. No. 09/396,331.

However, these patent applications do not make it possible to provide satisfactory solutions to the problems which may be encountered in combating or controlling insects which ravage crops, in particular by means of specific insecticidal processes.

One of the problems encountered in the protection of crops against harmful arthropods, and in particular insect pests, lies in the need to reduce the amounts of active ingredient used whilst allowing a satisfactory, if not greater, efficacy to be obtained. Indeed, it is common to broadcast or employ large amounts of the said insecticidal active ingredients.

Another problem encountered concerns the need to have available active ingredients which are effective against a broad spectrum of insect pests capable of damaging or damaging crops.

Another problem relates to the effect over time of the active ingredients employed for the protection of crops: it is desirable both to have active ingredients possessing an immediate, or virtually immediate, insecticidal activity following application to the crops, and also that these said active ingredients possess an insecticidal effect whose duration is sufficient to allow effective and lasting protection of the crops against insect pests.

Another problem lies in the fact that certain insecticidal active ingredients do not possess an immediate insecticidal effect but act only after a certain period of time has elapsed following application, thereby allowing the populations of insect pests to multiply before the active ingredient utilized takes effect.

Another problem encountered with a considerable number of insecticidal active ingredients is that they have only a curative effect, therefore obliging the user to undertake demanding and careful monitoring of the crops in order to determine the exact time of treatment.

Another problem of significance is that a number of insecticidal active ingredients have only a preventive effect, therefore forcing the user to broadcast amounts of these active ingredients which, subsequently, prove to be useless.

Another problem associated with the use of certain insecticidal active ingredients resides in the phenomenon of resurgence of the populations of insect pests treated, a phenomenon which is critical to the user, who initially sees the populations of harmful organisms reduced after treatment but then, subsequently, sees these populations grow again. Although this phenomenon of resurgence is not frequent, it is extremely damaging when it does occur.

Another problem which lies in the use of certain known insecticidal compounds is the difficulty of finding a means for effectively controlling a group of several insect pests liable to attack a specific crop.

In particular, it is especially difficult to provide a means of effective insecticidal control for a set of insect pests which ravage rice crops, especially a means of controlling insect pests of the families *Delphacidae, Noctuidae, Plutellidae, Pyralidae, Tortricidae*.

The numerous problems which have been set out above are very often accompanied by those associated with the protection of the environment, environmental problems to which the users of insecticidal active ingredients are more and more sensitive, as are the consumers of the products obtained from these crops.

Another difficulty in relation to the use of many insecticides lies in the cumulative effect of two or more of the problems which have been set out above. Indeed, it is even more difficult to solve the problems which have arisen when they accumulate, since the solutions which may be considered are in some cases contradictory or even conflictive.

Moreover, and of a general nature, it is always desirable to improve the spectrum of activity and the efficacy of compounds having an insecticidal action, or to reinforce the said spectra of activity and of efficacy, by combining the said compounds in order to obtain a higher-performance product or combination, as well as processes for combating or controlling insects which ravage crops, these processes being optimally tailored to the specific requirements of the users.

It is also desirable to prevent the appearance of resistances to these insecticides on the part of insect pests.

It is likewise always desirable to provide the user of these insecticidal compounds with an increased range of insecticidal means for combating or controlling insect pests, particularly in the field of agriculture, owing in particular to the devastation which these insect pests can wreak on crops.

It is likewise highly desirable to improve or better control the rate or persistency of action of these insecticidal compounds.

It is likewise always desirable to provide the user of these insecticidal compounds with means of combating or controlling insect pests under specific conditions of use, especially in accordance with the environment of the crops to be protected or in accordance with the crops or the insect pests damaging or damaging these crops, or alternatively according to the degree of infestation with these insect pests.

It is also most desirable to provide insecticidal control means which possess a so-called knockdown insecticidal effect, the said knockdown effect consisting, in the sense of the present text, in a rapid effect of the insecticidal action, usually measured by a rapid decrease in the number of insects. Such a knockdown effect is preferably recognized for active materials whose satisfactory insecticidal action appears within a few hours.

It is likewise desirable to allow a persistency of action over time of the insecticidal action of the insecticidal active ingredients employed.

The present invention therefore proposes to provide solutions to all or part of the many problems which have been set out above. The present invention also proposes to attain all or part of the objectives which have been referred to.

An essential aspect of the present invention relates to specific processes for treating and controlling crop-damaging arthropods, preferentially insecticidal processes, which use an insecticidal compound (A) containing a pyrazole group, and an insecticidal compound (B) of the pyrethroid family.

Preferentially, the processes according to the present invention are advantageously carried out in the agricultural sector, particularly for plant protection.

Advantageously, the protection or treatment processes according to the present invention use an insecticidal compound (A) of the phenylpyrazole family.

More advantageously, the said processes according to the invention use an insecticidal compound (A) of formula (I)

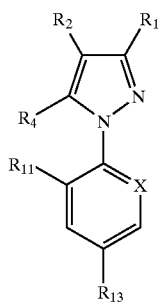

(I)

in which:
R$_1$ represents —CN or the methyl radical or the radical —C(S)NH$_2$ or the radical —C(=N—Y)Z;
R$_2$ represents —S(O)$_n$R$_3$;
R$_3$ represents an alkyl or haloalkyl radical;
R$_4$ is selected from the group consisting of a hydrogen atom, a halogen atom and a radical which can be —NR$_5$R$_6$, —C(O)OR$_7$, —S(O)$_m$R$_7$, alkyl, haloalkyl, —OR$_8$ or —N=C(R$_9$)(R$_{10}$);
R$_5$ and R$_6$ are selected independently from a hydrogen atom, an alkyl or haloalkyl radical, —C(O)alkyl, —C(O)OR$_7$ and —S(O)$_r$CF$_3$; or R$_5$ and R$_6$ together form a divalent radical which can be interrupted by one or more heteroatoms;
R$_7$ is selected from an alkyl radical and a haloalkyl radical;
R$_8$ is selected from an alkyl radical, a haloalkyl radical and a hydrogen atom;

R$_9$ is selected from a hydrogen atom and an alkyl radical;
R$_{10}$ is selected from a phenyl and heteroaryl radical optionally substituted with one or more hydroxyl radicals, halogen atoms, —O-alkyls, —S-alkyls, cyano or alkyl radicals or a combination thereof;
X is selected from the nitrogen atom and the radical C—R$_{12}$;
Y is selected from the hydroxyl, amino, aminocarbonyl, alkoxy, arylcarbonyl, alkylcarbonyl, alkoxycarbonyl, carbamoyl, arylcarbamoyl, alkylcarbamoyl and pyrazole groups, substituted or unsubstituted;
Z is selected from the hydroxyl, amino, aminocarbonyl, alkoxy, arylcarbonyl, alkylcarbonyl, alkoxycarbonyl, carbamoyl, arylcarbamoyl and alkylcarbamoyl groups;
R$_{11}$ and R$_{12}$ are selected independently from a halogen atom and a hydrogen atom;
R$_{13}$ is selected from a halogen atom, a haloalkyl or haloalkoxy radical, —S(O)$_q$CF$_3$ and —SF$_5$;
m, n, q and r are selected independently from 0, 1 and 2;
with the proviso that, if R$_1$ represents the methyl radical, then R$_3$ represents a haloalkyl radical, R$_4$ represents —NH$_2$, R$_{11}$ represents Cl, R$_{13}$ represents —CF$_3$ and X represents N;
the alkyl and alkoxy radicals of the formula (I) are preferably lower alkyl and alkoxy radicals, i.e. radicals possessing from one to four carbon atoms;
the haloalkyl and haloalkoxy radicals likewise possess preferably from one to four carbon atoms;
the haloalkyl and haloalkoxy radicals can carry one or more halogen atoms; the preferred radicals of this type comprise —CF$_3$ and —OCF$_3$.

According to one preferred variant, the processes according to the invention use an insecticidal compound (A) of formula (I) in which:
R$_1$ represents —CN; and/or
R$_4$ represents —NR$_5$R$_6$; and/or
R$_5$ and R$_6$ are selected independently from a hydrogen atom, an alkyl or haloalkyl radical and —C(O)alkyl; and/or
X represents —C—R$_{12}$; and/or
R$_{13}$ is selected from a halogen atom, a haloalkyl or haloalkoxy radical and —SF$_5$.

According to one especially advantageous variant, the protection or treatment processes according to the invention use Fipronil, chemical name 5-amino-3-cyano-1-(2,6-dichloro-4-trifluoromethylphenyl)-4-trifluoromethylsulphinylpyrazole, as insecticidal compound (A).

According to another advantageous embodiment of the processes according to the invention, the compound (B) used is a compound of formula (II)

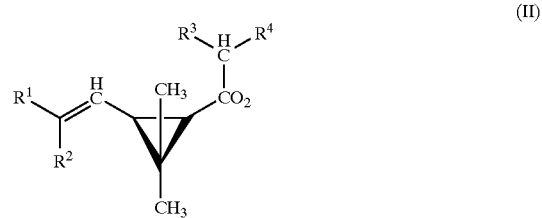

(II)

in which:
R$_1$ and R$_2$ represent, independently, a C$_1$ to C$_8$ alkyl radical or a C$_1$ to C$_8$ haloalkyl radical or a halogen atom or a substituted or unsubstituted phenyl group; and/or R₃ represents a —CN group or a hydrogen atom or a $C_1$ to $C_8$ alkyl radical; and/or R₄ represents a substituted or unsubstituted phenyl group.

According to another advantageous embodiment, the compound (B) used in the processes according to the invention is a compound of formula (II) in which:

R₁ and R₂ represent, independently, a bromine atom or a chlorine atom or a methyl radical or an isopropyl radical or a para-chlorophenyl radical or a trifluoromethyl radical; and/or R₄ represents a substituted or unsubstituted phenoxybenzyl group.

According to another advantageous embodiment, the compound (B) used for the processes according to the invention is a compound of formula (II) in which:

R₄ represents a halophenoxybenzyl group.

Where appropriate, and during its use in processes according to the invention, the compound (B) of formula (II) may be either in the form of a specific isomer or in the form of a mixture of several isomers, or even in the form of a mixture of several compounds of formula (II).

However, as regards the compounds of the pyrethroid family which are used as insecticidal compound (B) during the use of the protection or treatment processes according to the invention, the compounds preferably used are those chosen from the group comprising bifenthrin or 2-methylbiphenyl-3-ylmethyl-(Z)-(1RS, 3RS)-3-(2-chloro-3,3,3-trifluoroprop-1-enyl)-2,2-dimethylcyclopropanecarboxylate;

cyfluthrin or (R,S)-α-cyano-4-fluoro-3-phenoxybenzyl (1RS,3RS;1RS,3SR)-3-(2,2-dichlorovinyl)-2,2-dimethylcyclopropanecarboxylate;

cyhalothrin or (R,S)-α-cyano-3-phenoxybenzyl (Z)-(1RS, 3RS)-(2-chloro-3,3,3-trifluoropropenyl)-2,2-dimethylcyclopropanecarboxylate;

cypermethrin or (R,S)-α-cyano-3-phenoxybenzyl (1RS, 3RS;1RS,3SR)-3-(2,2-dichlorovinyl)-2,2-dimethylcyclopropanecarboxylate;

alpha-cypermethrin or racemic mixture comprising (S)-α-cyano-3-phenoxybenzyl (1R,3R)-3-(2,2-dichlorovinyl)-2,2-dimethylcyclopropanecarboxylate and (R)-α-cyano-3-phenoxybenzyl (1S,3S)-3-(2,2-dichlorovinyl)-2,2-dimethylcyclopropanecarboxylate;

beta-cypermethrin or reaction mixture comprising, in a 2:3 ratio, the 2 enantiomeric pairs (S)-α-cyano-3-phenoxybenzyl (1R)-cis-3-(2,2-dichlorovinyl)-2,2-dimethylcyclopropanecarboxylate and (R)-α-cyano-3-phenoxybenzyl (1S)-cis-3-(2,2-dichlorovinyl)-2,2-dimethylcyclopropanecarboxylate with (S)-α-cyano-3-phenoxybenzyl (1R)-trans-3-(2,2-dichlorovinyl)-2,2-dimethylcyclopropanecarboxylate and (R)-α-cyano-3-phenoxybenzyl (1S)-trans-3-(2,2-dichlorovinyl)-2,2-dimethylcyclopropanecarboxylate;

theta-cypermethrin or mixture of the enantiomers (R)-α-cyano-3-phenoxybenzyl (1S,3R)-3-(2,2-dichlorovinyl)-2,2-dimethylcyclopropanecarboxylate and (S)-α-cyano-3-phenoxybenzyl (1R,3S)-3-(2,2-dichlorovinyl)-2,2-dimethylcyclopropanecarboxylate in a 1:1 ratio;

zeta-cypermethrin or mixture of the stereoisomers (S)-α-cyano-3-phenoxybenzyl (1RS,3RS;1RS,3SR)-3-(2,2-dichlorovinyl)-2,2-dimethylcyclopropanecarboxylate, in which mixture the ratio of the enantiomeric pairs (S)-(1RS,3RS) and (S)-(1RS,3SR) is, respectively, between 45/55 and 55/45;

deltamethrin or (S)-α-cyano-3-phenoxybenzyl (1R,3R)-3-(2,2-dibromovinyl)-2,2-dimethylcyclopropanecarboxylate;

fenpropathrin or (RS)-α-cyano-3-phenoxybenzyl 2,2,3,3-tetramethylcyclopropanecarboxylate;

fenvalerate or (RS)-α-cyano-3-phenoxybenzyl (RS)-2-(4-chlorophenyl)-3-methylbutyrate;

flumethrin or α-cyano-4-fluoro-3-phenoxybenzyl;

permethrin or 3-phenoxybenzyl (1RS,3RS;1RS,3SR)-3-(2,2-dichlorovinyl)-2,2-dimethylcyclopropanecarboxylate;

phenothrin or 3-phenoxybenzyl (1RS,3RS;1RS,3SR)-2,2-dimethyl-3-(2-methylprop-1-enyl)-cyclopropanecarboxylate;

tefluthrin or 2,3,5,6-tetrafluoro-4-methylbenzyl (Z)-(1RS, 3RS)-3-(2-chloro-3,3,3-trifluoroprop-1-enyl)-2,2-dimethylcyclopropanecarboxylate;

tralomethrin or (S)-α-cyano-3-phenoxybenzyl (1R,3S)-2,2-dimethyl-3-[(RS)-1,2,2,2-tetrabromoethyl] cyclopropanecarboxylate;

flucythrinate or (RS)-α-cyano-3-phenoxybenzyl (S)-2-(4-difluoromethoxyphenyl)-3-methylbutyrate;

tau-fluvalinate or (RS)-α-cyano-3-phenoxybenzyl N-(2-chloro-α,α,α-trifluoro-p-tolyl)-D-valinate.

Moreover, the compounds of the pyrethroid family which may be used when carrying out the processes according to the invention are, for some of them, known per se as having certain insecticidal properties or as having insecticidal activity, while at the same time being acceptable for agricultural uses, in particular for treating or protecting crops.

In the different process variants according to the present invention, the insecticidal compounds (A) and (B) are used in effective but non-phytotoxic doses.

As regards the insecticidal compounds (A) containing a pyrazole group, which are used in the various processes according to the present invention, reference may also be made to those disclosed, respectively, in the European patents or patent applications EP-A-0 295 117, EP-A-0 460 940 or EP-A-0 484 165; as well as in International patent application WO 98/28279.

Reference may moreover be made to the book The Electronic Pesticide Manual version 1.0 (from the British Crop Protection Council, edited by Clive Tomlin) as regards processes for preparing the insecticidal compounds (B).

Except where otherwise mentioned and throughout the present text, the insecticidal compounds (A) and (B) used may be denoted, without preference, by any one of the following expressions: active materials or compounds or insecticidal compounds or active substances or insecticidal substances, without, however, departing from the spirit of the present invention, especially on account of the insecticidal properties of these compounds, substances or materials.

Preferably, and for their use in practise when carrying out the processes according to the present invention, the various insecticidal substances (A) and (B) described above are rarely used alone.

Thus, for their use in the processes according to the invention, the insecticidal active materials (A) and (B) are usually combined with a solid or liquid support, which can be used especially in the agricultural sector, and optionally with at least one surfactant and/or one or more auxiliary agents.

These processes according to the invention, which are useful in particular for protecting plants against insects, use as active material at least one of the insecticidal compounds (A) or (B) as described above, advantageously in combination with agriculturally acceptable solid or liquid supports and/or surfactants that are also agriculturally acceptable.

In particular, supports which may be used are the common inert supports; similarly, surfactants which may be used are the surfactants that are common in the formulation of compositions intended for agricultural use, in particular for treating or protecting crops, such as those of the present invention.

A more detailed description of the various compounds or adjuvants which, for the purposes of the present invention, may be combined with the compounds (A) and (B) will be the subject of a specific development later in the present text.

Usually, the processes according to the invention use formulations comprising between 0.00001% and 100%, preferably between 0.001% and 80%, of insecticidal compounds (A) and (B), whether these compounds are combined or are in the form of two active materials used separately.

Usually, however, the processes according to the invention combine an insecticidal compound (A) and an insecticidal compound (B) simultaneously.

Except where otherwise mentioned, the proportions and percentages used or described throughout the present description and in the claims which follow are proportions or percentages on a weight basis.

More generally, when they are used in the processes according to the invention, the insecticidal compounds (A) and (B) may be combined with any solid or liquid additive corresponding to the usual formulation techniques, particularly the formulation of products or compositions intended for uses or utilizations in agriculture.

Among the treatment and/or protection processes or methods according to the invention, the ones which are preferred are those which are used for treating and/or protecting crops.

The said use of the processes according to the invention can be carried out according to various forms and in particular using quite a wide variety of application methods, but also according to different application techniques, or alternatively to protect different types, varieties or families of vegetation or plants, or alternatively to combat or control different types or species of arthropods, especially insect pests.

As regards the various application methods carried out beneficially in the processes according to the invention, simultaneous, separate, alternating or sequential application methods are especially possible.

Usually, however, the application methods that are beneficial in the processes according to the invention and which are preferred consist of methods for applying the insecticidal compounds (A) and (B) simultaneously.

However, a relatively advantageous variant of a process according to the invention uses a method of alternate application of the insecticidal compounds (A) and (B).

Another application method which is useful for carrying out the processes according to the invention relates to the sequential application of the insecticidal compounds (A) and (B); such a sequential application method may especially take the form of several applications of insecticidal compound (A), followed by several applications of insecticidal compound (B). Needless to say, a reversed sequential application method consisting of several applications of insecticidal compound (B) followed by several applications of insecticidal compound (A) also forms a part of the processes of the present invention.

The different variants for carrying out the processes according to the invention which have just been described may also be combined or associated, in whole or in part, with one another. A person skilled in the art will readily know how to determine the associations or combinations of application methods according to the invention which best suit the use of the insecticidal compounds (A) and (B) which he envisages.

Besides the various methods for carrying out the processes according to the invention which have just been described, the said processes can also use a relatively large number of application techniques; thus, among the said techniques which may be mentioned in particular are dusting, dipping, spraying, smoking or misting, etc.

Other variants of the application methods that are useful for the processes according to the invention exist, particularly depending on the part(s) of the plant or vegetation which is (are) to be treated.

Thus, the processes according to the invention can be carried out for the treatment or protection of the plant propagation material or the seeds, in particular the grains, the tubers or the rhizomes; for the treatment of the roots, or for the treatment of the stems or leaves of the plant; as well as for the treatment of the roots, or alternatively of the fruits or other parts of the plant having a substantial economic or agronomic value.

Furthermore, the said processes according to the invention may be carried out for the treatment of plants at numerous stages in their development, in particular for the treatment of seeds, seedlings or planted-out seedlings, planted-out plants, or plants.

The processes which are carried out for the treatment of the soil under cultivation or to be cultivated also form a part of the present invention.

However, and in a particularly advantageous manner, the processes according to the invention use the insecticidal compounds (A) and (B) for treatment by foliar application to the plant to be treated. Even more advantageously, such a treatment is carried out by spraying.

Likewise, said processes according to the invention for seed treatment are particularly advantageous.

The processes for treating or protecting plants according to the invention by means of the insecticidal compounds (A) and (B) are particularly advantageous when carried out for the treatment or protection of cereal or market-garden crops, particularly rice, wheat, barley or rye, as well as for the treatment or protection of corn, sorghum, sunflower, soybean, or alternatively cotton, pea, rape, potato, vegetable or fruit crops, beet, onions, cabbages, tomatoes, beans, lettuces, etc.

The said processes for treating or protecting plants according to the invention give particularly advantageous results when used for the treatment of rice. Particularly advantageous results are obtained with numerous varieties of rice, whether or not these varieties are hybrid varieties. The processes according to the invention that are beneficially carried out for the treatment or protection of the variety *Oryza sativa* also give highly satisfactory results.

As may emerge from the preceding development of the present text, the processes according to the invention may be useful both for preventive treatments and for curative treatments.

The processes according to the invention using an insecticidal compound (A) and an insecticidal compound (B) are advantageously carried out to combat or control harmful arthropods, especially harmful insects.

Thus, the said processes according to the invention are advantageously employed for combating or controlling insects of the families *Delphacidae* sp., especially *Nilaparvata lugens, Nilaparvata oryzae* and *Sogatella furcifera*;

and/or *Cicadellidae* sp. especially *Empoasca decipiens, Nephotettix apicalisi, Nephotettix impicticeps, Nephotettix cincticeps* and *Nilaparvata oryzae*; and/or *Pyralidae* sp., especially *Tryporyza incertulas, Tryporyza innotata, Cnaphalocrosis medinalis, Chilo loftini, Chilo suppressalis, Chilo indicus* and *Chilotraea plejadellus*; *Tylenchidae* sp., especially *Ditylenchus dipsaci, Ditylenchus angustus* and *Ditylenchus radicicolus*; and/or *Noctuidae* sp., especially *Sesamia interens, Sesamia calamistis* and *Sesamia cretica*; and/or *Pentatomidae* sp. especially *Scotinophara lurida* and *Scotinophara coarctata*; and/or *Plutellidae* sp. especially *Plutella xylostella*; and/or *Tortricidae* sp. especially *Archips breviplicanus*; and/or *Cecidomyiidae* sp. especially *Orselia oryzae* and *Pachydiplosis oryzae*.

According to another way of working the processes according to the invention, they are advantageously carried out for combating or controlling soil borne insect pests and notably those where at least one living stage is in the soil and during this stage cause damages to crops.

Thus, among such soil borne insect pests can be mentioned *Aeneolamia* sp., *Agrotis* sp., *Agriotes* sp., *Araecerus* sp., *Aulacophora* sp., *Atherigona* sp., *Cerotoma* sp., *Chilo* sp., *Cylas* sp., *Delia* sp., *Diabrotica* sp., *Diaprepes* sp., *Elasmopalpus* sp., *Frankliniella* sp., *Graphognathus* sp., *Gryllotalpa* sp., *Hypomeces* sp., *Heteronychus* sp., *Holotrichia* sp., *Hydraecia* sp., *Hylemia* sp., *Leucopholis* sp., *Lepidiota* sp., *Limonius* sp., *Listroderes* sp., *Loxostege* sp., *Mamestra* sp., *Melolontha* sp., *Oscinella* sp., *Ostrinia* sp., *Otiorhynchus* sp., *Phyllophaga* sp., *Phyllotreta* sp., *Popillia* sp., *Pseudococcus* sp., *Psila* sp., *Psylloides* sp., *Sitona* sp., *Spoladea* sp., *Tanymecus* sp., *Thrips* and *Tribolium* sp.

Or even, processes according to the invention are very advantageous:

against lepidopterans, notably *Pectinophora gossypiella, Bupalus piniarius, Cheimatobia brumata, Lithocolletis blancardella, Hyponomeuta padella, Plutella* sp., e.g. *Plutella xylostella, Malacosoma neustria, Euproctis chrysorrhoea, Lymantria* sp., e.g. *Bucculatrix thurberiella, Phyllocnistis citrella, Agrotis* sp., e.g. *Agrotis segetum, Agrotis ipsilon, Euxoa* sp., *Feltia* sp., *Earias insulana, Heliothis* sp., e.g. *Helicoverpa armigera, Helicoverpa armigera, Helicoverpa zea, Laphygma exigua, Mamestra brassicae, Panolis flammea, Prodenia litura, Spodoptera* sp., e.g. *Spodoptera littoralis, Spodoptera litura, Spodoptera exigua, Trichoplusia ni, Cydia pomonella, Pieris* sp., *Chilo* sp., e.g. *Chilo suppressalis, Pyrausta nubilalis, Ephestia kuehniella, Galleria mellonella, Cacoecia podana, Capua reticulana, Choristoneura fumiferana, Clysia ambiguella, Hofmannophila pseudospretella, Homona magnanima, Tineola bisselliella, Tinea pellionella, Elasmopalpus* sp., *Hydraecia* sp., *Loxostege* sp., *Ostrinia* sp., *Spoladea* sp., e.g. *Tortrix viridana*;

against coleopterans, notably *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* sp., e.g. *Diabrotica undecimpunctata, Diabrotica virgifera, Psylloides chrysocephala, Epilachna varivestis, Atomaria* sp., e.g. *Atomaria linearis, Oryzaephilus surinamensis, Anthonomus* sp., e.g. *Anthonomus grandis, Otiorhynchus sulcatus, Cosmopolites sordidus, Ceuthorrynchus assimilis, Hypera postica, Dermestes* sp., *Trogoderma* sp., *Anthrenus* sp., *Attagenus* sp., *Lyctus* sp., e.g. *Meligethes aeneus, Ptinus* sp., e.g. *Niptus hololeucus, Gibbium psylloides, Tribolium* sp., e.g. *Tenebrio molitor, Agriotes* sp., e.g. *Agriotes lineatus, Conoderus* sp., e.g. *Melolontha melolontha, Amphimallon solstitialis, Aeolus* sp., *Araecerus* sp., *Aulacophora* sp., *Cerotoma* sp., *Chaetocnema* sp., *Cylas* sp., *Diaprepes* sp., *Graphognathus* sp., *Heteronychus* sp., *Holotrichia* sp., *Hypomeces* sp., *Leucopholis* sp., *Lepidiota* sp., *Limonius* sp., *Listroderes* sp., *Melanotus* sp., *Phyllotreta* sp., *Phyllophaga* sp., *Popillia* sp., *Sitona* sp., *Tanymecus* sp., e.g. *Costelytra zealandica* or against dipterans and notably *Drosophila melanogaster, Chrysomyxa* sp., *Hypoderma* sp., *Tannia* sp., *Bibio hortulanus, Oscinella frit, Phorbia* sp., *Pegomyia hyoscyami, Ceratitis capitata, Dacus oleae, Tipula* sp., *Tipula paludosa, Atherigona* sp., *Delia* sp., *Hylemia* sp., *Psila rosae, Tipula oleracea*.

According to a preferred use of the processes according to the invention, these processes are carried out to simultaneously combat several of the insect pests mentioned; in this case, the processes are referred to as processes for controlling a group of damaging insects.

According to an even more preferred use, such processes for controlling or treating a group of damaging insects are carried out for the treatment or protection of a given crop.

Even more preferably, the processes according to the invention are carried out in processes for controlling or treating insects, which ravage rice crops.

The processes for controlling or combating the insect pests according to the invention may be carried out at the various stages in the life or development of the insects, in particular to control the eggs, the larvae, irrespective of their stage of development, the chrysalides or the nymphs, or alternatively to control the arthropods or the insects at the adult stage.

Moreover, the said processes may be carried out both against isolated insects and against colonies of the said insects, as well as during infestations with the said insects.

For their use in treatment or protection processes according to the invention, the insecticidal compounds (A) and (B) are used in amounts which may vary within a wide range, especially according to the type of crop and according to the virulence, nature and degree of the attack by the insects, and also according to the climatic or soil conditions.

Advantageously, in the treatment or protection processes according to the invention, the insecticidal compound (A), preferably Fipronil, is used in an amount ranging from 0.5 to 500 g/ha, preferably ranging from 2 to 100 g/ha; as regards the insecticidal compound (B), which is preferably one of the compounds chosen from bifenthrin, cyfluthrin, cyhalothrin, cypermethrin, alpha-cypermethrin, beta-cypermethrin, theta-cypermethrin, zeta-cypermethrin, deltamethrin, fenpropathrin, fenvalerate, flumethrin, permethrin, phenothrin, tefluthrin, tralomethrin, flucythrinate and tau-fluvalinate, it is used in an amount ranging from 0.5 to 1000 g/ha, preferably ranging from 1 to 500 g/ha.

Even more advantageously, in the treatment or protection processes according to the invention, the insecticidal compounds (A) and (B) are used simultaneously in respective amounts of between 2 and 100 g/ha for the insecticidal compound (A) and between 1 and 500 g/ha for the insecticidal compound (B).

The weight ratio A/B is generally between 0.0005 and 250, preferably between 0.05 and 10; the weight ratio B/A is, for its part, generally between 0.004 and 2000, preferably between 0.1 and 20.

As has just been pointed out, the ratio A/B is a weight ratio of the amounts of insecticidal compounds (A) and (B) used.

Where appropriate, and in a most preferred manner, in the processes according to the invention, the ratio between the amounts of fipronil and of deltamethrin used is between 0.1 and 5, preferably between 0.5 and 3; similarly, the ratio between the amounts of fipronil and of cypermethrin is between 0.05 and 10, preferably between 0.15 and 6.

As regards the amounts of insecticidal compounds (A) and (B) used in the treatment or protection processes according to the invention by foliar application, particularly satisfactory results are obtained for applications after dilution, in particular in water, of between 50 and 1500 l/ha, preferably between 200 and 800 l/ha.

For their use in the treatment or protection processes according to the present invention, the insecticidal compounds (A) and (B) may be applied simultaneously, but may also be prepared extemporaneously at the time of use of the said processes according to the invention.

According to another embodiment of the said processes according to the invention, the insecticidal compounds (A) and (B) can also be applied separately.

Another aspect of the present invention relates to insecticidal compounds, which may be used in the processes according to the invention which have been the subject of the above developments.

In a particularly advantageous manner, the compositions according to the invention comprise an insecticidal compound (A) and an insecticidal compound (B) as have been defined above.

Thus, the compositions according to the invention preferably comprise an insecticidal compound (A) containing a pyrazole group, and an insecticidal compound (B) from the pyrethroid family.

The compositions according to the present invention advantageously comprise an insecticidal compound (A) from the phenylpyrazole family.

More advantageously, the said compositions according to the invention comprise an insecticidal compound (A) of formula (I) in which:

$R_1$ represents —CN or the methyl radical or the radical —C(S)NH$_2$ or the radical —C(=N—Y)Z;

$R_2$ represents —S(O)$_n$R$_3$;

$R_3$ represents an alkyl or haloalkyl radical;

$R_4$ is selected from the group consisting of a hydrogen atom, a halogen atom and a radical which can be —NR$_5$R$_6$, —C(O)OR$_7$, —S(O)$_m$R$_7$, alkyl, haloalkyl, —OR$_8$ or —N=C(R$_9$)(R$_{10}$);

$R_5$ and $R_6$ are selected independently from a hydrogen atom, an alkyl or haloalkyl radical, —C(O)alkyl, —C(O)OR$_7$ and —S(O)$_r$CF$_3$; or $R_5$ and $R_6$ together form a divalent radical which can be interrupted by one or more heterbatoms;

$R_7$ is selected from an alkyl radical and a haloalkyl radical;

$R_8$ is selected from an alkyl radical, a haloalkyl radical and a hydrogen atom;

$R_9$ is selected from a hydrogen atom and an alkyl radical;

$R_{10}$ is selected from a phenyl radical and heteroaryl radical optionally substituted with one or more hydroxyl radicals, halogen atoms, —O-alkyls, —S-alkyls, cyano or alkyl radicals or a combination thereof;

X is selected from the nitrogen atom and the radical C—$R_{12}$;

Y is selected from the hydroxyl, amino, aminocarbonyl, alkoxy, arylcarbonyl, alkylcarbonyl, alkoxycarbonyl, carbamoyl, arylcarbamoyl, alkylcarbamoyl and pyrazole groups, substituted or unsubstituted;

Z is selected from the hydroxyl, amino, aminocarbonyl, alkoxy, arylcarbonyl, alkylcarbonyl, alkoxycarbonyl, carbamoyl, arylcarbamoyl and alkylcarbamoyl groups;

$R_{11}$ and $R_{12}$ are selected independently from a halogen atom and a hydrogen atom;

$R_{13}$ is selected from a halogen atom, a haloalkyl or haloalkoxy radical, —S(O)$_q$CF$_3$ and —SF$_5$;

m, n, q and r are selected independently from 0, 1 and 2;

with the proviso that, if $R_1$ represents the methyl radical, then $R_3$ represents a haloalkyl radical, $R_4$ represents —NH$_2$, $R_{11}$ represents Cl, $R_{13}$ represents —CF$_3$ and X represents N;

the alkyl and alkoxy radicals of the formula (I) are preferably lower alkyl and alkoxy radicals, i.e. radicals possessing from one to four carbon atoms;

the haloalkyl and haloalkoxy radicals likewise possess preferably from one to four carbon atoms;

the haloalkyl and haloalkoxy radicals can carry one or more halogen atoms; the preferred radicals of this type comprise —CF$_3$ and —OCF$_3$.

According to another preferred embodiment, the compositions according to the invention comprise an insecticidal compound (A) of formula (I) in which:

$R_1$ represents —CN; and/or $R_4$ represents —NR$_5$R$_6$; and/or $R_5$ and $R_6$ are selected independently from a hydrogen atom, an alkyl or haloalkyl radical, —C(O)alkyl and C(O)OR$_7$; and/or X represents —C—$R_{12}$; and/or $R_{13}$ is selected from a halogen atom, a haloalkyl or haloalkoxy radical and —SF$_5$.

In accordance with another especially advantageous embodiment, the compositions according to the invention comprise Fipronil, chemical name 5-amino-3-cyano-1-(2,6-dichloro-4-trifluoromethylphenyl)-4-trifluoromethylsulphinylpyrazole, as insecticidal compound (A).

As regards the compounds of the pyrethroid family which are usually used as insecticidal compound (B) in the compositions according to the invention, the ones preferably used are those of formula (II) in which:

$R_1$ and $R_2$ represent, independently, a $C_1$ to $C_8$ alkyl radical or a $C_1$ to $C_8$ haloalkyl radical or a halogen atom or a substituted or unsubstituted phenyl group;

$R_3$ represents a —CN group or a hydrogen atom or a $C_1$ to $C_8$ alkyl radical;

$R_4$ represents a substituted or unsubstituted phenyl group.

Advantageously and according to another embodiment of the compositions according to the invention, the compound (B) used is a compound of formula (II) in which:

$R_1$ and $R_2$ represent, independently, a bromine atom or a chlorine atom or a methyl radical or an isopropyl radical or a para-chlorophenyl radical or a trifluoromethyl radical; and/or $R_4$ represents a substituted or unsubstituted phenoxybenzyl group.

Another advantageous embodiment of the compositions according to the invention uses a compound (B) of formula (II) in which:

$R_4$ represents a halophenoxybenzyl group.

Where appropriate, and in the compositions according to the invention, the compound (B) of formula (II) can be used either in the form of a specific isomer or in the form of a mixture of several isomers, or even in the form of a mixture of several compounds of formula (II).

However, as regards the compounds of the pyrethroid family which are used as insecticidal compound (B) in the compositions according to the invention, the ones preferably used are the compounds chosen from the group comprising:

bifenthrin or 2-methylbiphenyl-3-ylmethyl-(Z)-(1RS, 3RS)-3-(2-chloro-3,3,3-trifluoroprop-1-enyl)-2,2-dimethylcyclopropanecarboxylate, especially in an A/B ratio of between 0.25 and 0.9;

cyfluthrin or (R,S)-α-cyano-4-fluoro-3-phenoxybenzyl (1RS,3RS;1RS,3SR)-3-(2,2-dichlorovinyl)-2,2-dimethylcyclopropanecarboxylate, especially in an A/B ratio of between 0.25 and 0.9;

cyhalothrin or (R,S)-α-cyano-3-phenoxybenzyl (Z)-(1RS, 3RS)-(2-chloro-3,3,3-trifluoropropenyl)-2,2-dimethylcyclopropanecarboxylate, especially in an A/B ratio of between 0.1 and 5;

cypermethrin or (R,S)-α-cyano-3-phenoxybenzyl (1RS, 3RS;1RS,3SR)-3-(2,2-dichlorovinyl)-2,2-dimethylcyclopropanecarboxylate, especially in an A/B ratio of between 0.25 and 0.9;

alpha-cypermethrin or racemic mixture comprising (S)-α-cyano-3-phenoxybenzyl (1R,3R)-3-(2,2-dichlorovinyl)-2,2-dimethylcyclopropanecarboxylate and (R)-α-cyano-3-phenoxybenzyl (1S,3S)-3-(2,2-dichlorovinyl)-2,2-dimethylcyclopropanecarboxylate;

beta-cypermethrin or reaction mixture comprising, in a 2:3 ratio, the 2 enantiomeric pairs (S)-α-cyano-3-phenoxybenzyl (1R)-cis-3-(2,2-dichlorovinyl)-2,2-dimethylcyclopropanecarboxylate and (R)-α-cyano-3-phenoxybenzyl (1S)-cis-3-(2,2-dichlorovinyl)-2,2-dimethylcyclopropanecarboxylate with (S)-α-cyano-3-phenoxybenzyl (1R)-trans-3-(2,2-dichlorovinyl)-2,2-dimethylcyclopropanecarboxylate and (R)-α-cyano-3-phenoxybenzyl (1S)-trans-3-(2,2-dichlorovinyl)-2,2-dimethylcyclopropanecarboxylate;

theta-cypermethrin or mixture of the enantiomers (R)-α-cyano-3-phenoxybenzyl (1S,3R)-3-(2,2-dichlorovinyl)-2,2-dimethylcyclopropanecarboxylate and (S)-α-cyano-3-phenoxybenzyl (1R,3S)-3-(2,2-dichlorovinyl)-2,2-dimethylcyclopropanecarboxylate in a 1:1 ratio;

zeta-cypermethrin or mixture of the stereoisomers (S)-α-cyano-3-phenoxybenzyl (1RS,3RS;1RS,3SR)-3-(2,2-dichlorovinyl)-2,2-dimethylcyclopropanecarboxylate, in which mixture the ratio of the enantiomeric pairs (S)-(1RS,3RS) and (S)-(1RS,3SR) is, respectively, between 45/55 and 55/45;

deltamethrin or (S)-α-cyano-3-phenoxybenzyl (1R,3R)-3-(2,2-dibromovinyl)-2,2-dimethylcyclopropanecarboxylate;

fenpropathrin or (RS)-α-cyano-3-phenoxybenzyl 2,2,3,3-tetramethylcyclopropanecarboxylate, especially in a ratio of between 0.1 and 5;

fenvalerate or (RS)-α-cyano-3-phenoxybenzyl (RS)-2-(4-chlorophenyl)-3-methylbutyrate, especially in a ratio of between 0.15 and 0.45;

flumethrin or α-cyano-4-fluoro-3-phenoxybenzyl;

permethrin or 3-phenoxybenzyl (1RS,3RS;1RS,3SR)-3-(2,2-dichlorovinyl)-2,2-dimethylcyclopropanecarboxylate, especially in a ratio of between 0.1 and 0.8;

phenothrin or 3-phenoxybenzyl (1RS,3RS;1RS,3SR)-2,2-dimethyl-3-(2-methylprop-1-enyl)-cyclopropanecarboxylate;

tefluthrin or 2,3,5,6-tetrafluoro-4-methylbenzyl (Z)-(1RS, 3RS)-3-(2-chloro-3,3,3-trifluoroprop-1-enyl)-2,2-dimethylcyclopropanecarboxylate, especially in a ratio of between 0.1 and 5;

tralomethrin or (S)-α-cyano-3-phenoxybenzyl (1R,3S)-2,2-dimethyl-3-[(RS)-1,2,2,2-tetrabromoethyl]-cyclopropanecarboxylate, especially in a ratio of between 0.6 to 0.9;

flucythrinate or (RS)-α-cyano-3-phenoxybenzyl (S)-2-(4-difluoromethoxyphenyl)-3-methylbutyrate;

tau-fluvalinate or (RS)-α-cyano-3-phenoxybenzyl N-(2-chloro-α,α,α-trifluoro-p-tolyl)-D-valinate.

Usually, the insecticidal compounds (A) and (B) used in the compositions according to the invention are combined with one or more supports and/or with one or more substances that are useful for formulating them. Thus, where appropriate, the compositions according to the invention can comprise up to 99% of support and/or up to 25% of one or more surfactants and/or up to 25% of one or more formulation agents.

Usually also, the compositions according to the invention comprise between 0.00001% and 100%, preferably between 0.001% and 80%, of insecticidal compounds (A) and (B), whether these compounds are combined, or whether they are in the form of two active materials used separately.

When they use two active materials (A) and (B) together, the said compositions according to the invention can do so in amounts as described above, but also for ratios A/B of between 0.0005 and 250, preferably between 0.05 and 10.

For their use in the compositions according to the invention, the compounds (A) and (B) are usually combined with one or more supports, optionally with one or more surfactants and optionally with one or more formulation agents or auxiliaries.

In the present description, the term "support" denotes an organic or mineral, natural or synthetic material with which the active material(s) (A) and/or (B) are [lacuna] in the compositions according to the invention, especially to facilitate their application to a plant, or alternatively to seeds or to the soil.

This support is thus generally inert and it should, usually, be agriculturally acceptable, in particular to the treated plant.

The support which may be used for the formulation of the compounds (A) and/or (B) in the processes according to the invention may be solid or liquid.

As examples of solid supports which may be used, mention may be made of natural or synthetic silicates, resins, waxes, fine powders or granules of clay, in particular of kaolin clay, of diatomaceous earth, of bentonite or of acidic clay, synthetic hydrated silicon oxide, talcs, ceramics, other minerals including sericite, quartz, sulphur, active charcoal, calcium carbonate and hydrated silica, or industrial fertilizers such as ammonium sulphate, ammonium phosphate, ammonium nitrate, urea or ammonium chloride.

As examples of liquid supports which may be used, mention may be made of water, alcohols and especially methanol or ethanol, ketones and especially acetone, methyl ethyl ketone or cyclohexanone, petroleum fractions, aromatic hydrocarbons including benzene, toluene, xylene, ethylbenzene or methylnaphthalene, non-aromatic hydrocarbons including hexane, cyclohexane, kerosene or gas oil, liquefied gas, esters including ethyl acetate and butyl acetate, nitriles including acetonitrile and isobutyronitrile, ethers including diisopropyl ether and dioxane, amides including N,N-dimethylformamide and N,N-dimethylacetamide, halogenated hydrocarbons including dichloromethane, trichloroethane and carbon tetrachloride, dimethyl sulphoxide, and plant oils including soybean oil and cotton oil.

The surfactant(s) may be emulsifiers, dispersants or wetting agents of ionic or nonionic type.

Mention may be made, for example, of polyacrylic acid salts, lignosulphonic acid salts, phenolsulphonic acid salts or naphthalenesulphonic acid salts, polycondensates of ethylene oxide with fatty alcohols or fatty acids or fatty amines, substituted phenols, in particular alkylphenols or arylphenols, salts of sulphosuccinic acid esters, taurine derivatives, in particular alkyltaurates, polyoxyethylated phosphoric esters of alcohols or of phenols; mention may be made most particularly of the salts of alkylsulphonates, alkylarylsulphonates, alkylaryl ethers, polyoxyethylenic derivatives thereof, polyethylene glycol ethers, polyalcohol esters, sugar derivatives, alcohols and the like.

The presence of at least one surfactant is generally essential when at least one of the active materials and/or the inert support is insoluble, especially in water when the vector agent for the application is water.

In the compositions according to the invention all kinds of other ingredients or agents may also be combined with the compounds (A) and/or (B) such as, for example, protective colloids, adhesives, thickeners, thixotropic agents, penetrating agents, stabilizers including isopropyl hydrogen phosphate, 2,6-di-tert-butyl-4-methylphenol, 2-tert-butyl-4-methoxyphenol and 3-tert-butyl-4-methoxyphenol, mineral or plant oils, fatty acids or esters thereof, sequestering agents, dispersants including casein, gelatin, saccharides and in particular starch powder, gum arabic, certain cellulose derivatives or alginic acid, lignin derivatives, bentonite, water-soluble synthetic polymers, in particular polyvinyl alcohol, polyvinylpyrrolidone, polyacrylic acids, etc., and also other active materials known for their pesticidal properties, in particular insecticides or fungicides; or for their properties of promoting plant growth, especially fertilizers; or for their regulatory properties on plant or insect growth.

The insecticidal compositions according to the invention may take quite a wide variety of forms, and may especially be in solid or liquid forms.

Thus, the said compositions according to the invention can take the form of relatively numerous formulations, among which mention may be made of oily solutions, emulsifiable concentrates, wettable powders, fluid formulations and especially aqueous suspensions or aqueous emulsions, granules, powders, aerosols, fumigenic formulations including self-combustible fumigenic formulations or fumigenic formulations involving a chemical reaction, formulations for nebulization, in particular formulations for misting, formulations with a very low volume, pastes, emulsions, concentrated suspensions, and also possible mixtures, associations or combinations of these various forms.

Usually, for the formulations such as the powders for dusting or dispersion, the content of insecticidal compounds (A) and (B) can be up to 100%; similarly, for the formulations in the form of granules, especially those obtained by extrusion, compacting, impregnation of a granular support or granulation using a powder, the content of insecticidal compounds (A) and (B) in these granules according to the invention is usually between 0.5% and 80%.

The insecticidal compositions according to the invention, referred to as concentrated compositions, comprising an insecticidal compound (A) and an insecticidal compound (B) which are in the form of emulsifiable concentrates or soluble concentrates, usually comprise from 25% to 100% of active materials; the ready-to-apply emulsions or solutions themselves contain from 0.00001% to 20% of active materials.

It goes without saying that the expression "active materials" should be understood throughout the present description as, where appropriate, an active material or insecticidal compound (A) or (B) alone, but also as a combination of these two active materials.

In addition to the solvent, the emulsifiable concentrates may contain, when necessary, 2% to 20% of suitable additives such as the stabilizers, surfactants, penetrating agents, corrosion inhibitors, colorants or adhesives mentioned above.

The insecticidal compositions according to the invention in the form of concentrated suspensions, which can also be applied by spraying, are prepared so as to obtain a stable fluid product which does not sediment out; they usually contain from 2% to 75% of active materials, from 0.5% to 15% of surfactants, from 0.1% to 10% of thixotropic agents, from 0% to 10% of suitable additives, such as antifoams, corrosion inhibitors, stabilizers, penetrating agents and adhesives, and, as support, water or an organic liquid in which the active material(s) is(are) insoluble or only sparingly soluble, or alternatively mixtures of several of these organic or inorganic solvents.

Certain solid organic materials or mineral salts may be dissolved in the support to halt or prevent the sedimentation; or alternatively such materials may be used as antifreezes for the water.

The insecticidal compositions according to the invention which take the form of wettable powders or powders for spraying are usually prepared such that they contain from 20% to 95% of active materials.

Moreover, they usually contain, besides a solid support, from 0% to 5% of a wetting agent, from 3% to 10% of a dispersant, and, where appropriate, from 0% to 10% of one or more stabilizers and/or other additives, such as penetrating agents, adhesives, anticaking agents, colorants, etc.

To obtain these powders for spraying or wettable powders, the active material(s) is(are) intimately mixed in suitable mixers with the additional substances, and are ground using mills or other suitable grinders. Powders for spraying are thus obtained with particularly advantageous wettability and suspendability; they can be suspended in water to any desired concentration.

Rather than wettable powders, it is possible to prepare insecticidal compositions according to the invention which are in the form of pastes.

The conditions and modes of preparation and of use of these pastes are similar to those for the wettable powders or powders for spraying.

As has just been stated, the aqueous dispersions and emulsions, for example the insecticidal compositions obtained by diluting a wettable powder or an emulsifiable concentrate according to the invention with water, are included in the general scope of the present invention.

The emulsions may be of the water-in-oil or oil-in-water type and they may have a thick or relatively thick consistency.

More generally, the compositions according to the invention may be in numerous formulation forms; thus, it is possible to use these compositions comprising an insecticidal compound (A) and an insecticidal compound (B) as an aerosol generator; lure (ready-to-use); concentrate for preparing lures; stock lure; capsule suspension; cold-nebulization product; powder for dusting; emulsifiable concentrate; emulsion of aqueous/aqueous type; emulsion of oily/reverse type; encapsulated granule; fine granule; concentrated suspension for seed treatment; compressed gas; gas-generating product; lure on grain; granulated lure; granule; hot-nebulization product; macrogranule; microgranule; powder to be dispersed in oil; concentrated suspension dilutable in oil; oil-miscible liquid; paste; stick for agropharmaceutical use; lure on bricks; powder for dry-treating seeds; lure on chunks; treated or coated seeds; fumigenic candle; fumigenic cartridge; fumigen; fumigenic granule; fumigenic stick; fumigenic tablet, fumigenic dish; soluble concentrate; soluble powder; liquid for treating seeds; concentrated suspension (=fluidizable concentrate); lain powder; very-low-volume liquid for application; very-low-volume suspension for application; vapour-diffuser product; granules or tablets to be dispersed in water; wettable powder for wet treatment; water-soluble granules or tablets; soluble powder for seed treatment; wettable powder.

According to another embodiment of the present invention, the various insecticidal compositions according to the invention which it has been possible to describe above may also take the form of extemporaneous mixtures, commonly referred to as tank mixes.

These insecticidal compositions in the form of tank mixes are usually in the form of dilute insecticidal compositions.

In this case, the insecticidal compositions according to the invention are in the form of insecticidal compositions separately comprising the insecticidal compounds (A) and (B), the said insecticidal compositions thus needing to be mixed together when they are applied or when the dilute insecticidal composition to be applied is prepared.

These insecticidal compositions known as tank mixes are usually mixed in the tank of the application device.

However, these said insecticidal compositions separately comprising the insecticidal compounds (A) and (B) may also be applied separately, in particular after dilution, thus making it possible to obtain the properties of the insecticidal compositions according to the invention comprising the said insecticidal compounds (A) and (B) directly on the sites of application.

It goes without saying that the different variants or embodiments which may be envisaged both for the compositions and for the treatment and/or protection processes according to the invention form an integral part of the present invention; the said different variants may moreover be combined or associated with each other without, however, departing from the spirit or scope of the said invention.

In the same manner, the various aspects of the present invention which have just been described may be combined or associated with each other without, however, departing from the spirit or scope of the said invention.

The examples which follow will allow a better illustration of the various aspects of the present invention, in particular of the aspects relating to the processes and to the compositions according to the invention using the said insecticidal compositions. However, these examples do not in any way limit the scope of the present invention.

The process examples A to L which follow will give an illustration of specific processes according to the invention.

These process examples will also make it possible to highlight many advantages intrinsic to the processes according to the invention.

PROCESS EXAMPLE A

This process example proposes to give an illustration of an insecticidal treatment process according to the invention.

The treatment process carried out was a treatment process against yellow rice stem borer or *Tryporyza incertulas* during the infestation of a rice crop. For the comparison of the process according to the invention with known insecticidal treatment processes, four plots were prepared in a similar manner.

The first is left without treatment, the second is treated with fipronil as active material, the third with deltamethrin and the fourth with fipronil and deltamethrin in accordance with the process according to the invention.

After sowing and then growing, the rice seedlings are transplanted at the three- to four-leaf stage.

The various active materials were then applied 7 days after planting out.

The formulation used in this process according to the invention is identical to that of Composition Example A.

The application rates and the results obtained are collated in Table 1.

The measurement was carried out by counting the number of rice plant cores that were dead due to attack by the damaging insects treated, i.e. *Tryporyza incertulas*; thus, the smallest number is obtained after carrying out the process according to the invention, while the untreated plots or plots treated in a known manner give substantially larger numbers.

These results thus show that the process according to the invention has better insecticidal efficacy while at the same time allowing a substantial reduction in the amounts of active materials spread and, concomitantly, a reduction in the environmental impact.

TABLE 1

|  | Plot No. 1 | Plot No. 2 | Plot No. 3 | Plot No. 4 |
|---|---|---|---|---|
| Active material used in the process carried out | No treatment | fipronil | deltamethrin | fipronil and deltamethrin |
| Rate of application of active material in the process | / | 10 g/ha | 6 g/ha | 11 g/ha of which 5 g/ha of fipronil and 6 g/ha of deltamethrin |
| Proportion of dead plant cores found | 78% | 56% | 66% | 54% |

This process example thus gives a perfect illustration of the advantages arising from the use of the process according to the invention, in particular on account of the very satisfactory insecticidal efficacy against the damaging insect treated, but also on account of the reduction in the amounts of active materials spread.

PROCESS EXAMPLE B

This process example gives an illustration of a process according to the invention which is useful for insecticidal treatment against leafhoppers and in particular against *Nephotettix apicalis*.

This process according to the invention was carried out for the treatment of a rice crop.

The operating conditions were reproduced and adapted from those of Process Example A.

The active materials used were fipronil and deltamethrin in a formulation in the form of granules according to Composition Example A.

The active material(s) was(were) applied to the plots 25 days after planting out.

The rates of active materials applied and the results obtained 14 days after application are collated in Table 2.

TABLE 2

|  | Plot No. 1 | Plot No. 2 | Plot No. 3 |
|---|---|---|---|
| Active material used in the process carried out | fipronil | deltamethrin | fipronil and deltamethrin |
| Rate of application of active material in the process | 25 g/ha | 6 g/ha | 11 g/ha of which 5 g/ha of fipronil and 6 g/ha of deltamethrin |
| Insecticidal efficacy | 16% | 6% | 28% |

The results obtained during the use of this process according to the invention are thus particularly satisfactory, both in terms of insecticidal efficacy and in terms of reduction in the amount of active material spread.

PROCESS EXAMPLE C

This process example gives an illustration of a process according to the invention which is useful for insecticidal treatment against *Nilaparvata lugens*. The operating and measuring conditions are reproduced and adapted from Process Example B.

The application rates and the results are collated in Table 3.

TABLE 3

|  | Plot No. 1 | Plot No. 2 | Plot No. 3 |
|---|---|---|---|
| Active material used in the Process carried out | fipronil | cypermethrin | fipronil and cypermethrin |
| Rate of application of active material in the process | 10 g/ha | 12.5 g/ha | 17.5 g/ha of which 5 g/ha of fipronil and 12.5 g/ha of cypermethrin |
| Insecticidal efficacy | 78% | 21% | 76% |

The results obtained during the use of this process according to the invention are thus particularly satisfactory, both in terms of insecticidal efficacy and in terms of reduction in the amounts of active materials spread.

PROCESS EXAMPLE D

This process example according to the invention gives an illustration of the improvement in the yield of a rice crop obtained concomitantly with the control of the insects which ravage this rice crop.

In this treatment Process Example according to the invention, the yield of the crop was evaluated, along with the improvement in this yield obtained by carrying out the said process according to the invention simultaneously using fipronil as compound (A) and cypermethrin as compound (B).

The operating and measuring conditions are reproduced and adapted from Process Example B.

The application rates and the results are collated in Table 4.

TABLE 4

|  | Plot No. 1 | Plot No. 2 | Plot No. 3 | Plot No. 4 |
|---|---|---|---|---|
| Active material used in the process carried out | fipronil | cypermethrin | fipronil and cypermethrin | No treatment |
| Rate of application of active material in the process | 10 g/ha | 12.5 g/ha | 17.5 g/ha of which 5 g/ha of fipronil and 12.5 g/ha of cypermethrin | / |
| Yield of the plot (kg/ha) | 2.276 | 1.416 | 2.596 | 791 |
| Improvement in the yield of the plot (%) | 188 | 78 | 228 | / |

The results obtained during the use of this process according to the invention are thus particularly satisfactory, both in terms of absolute yield and in terms of relative yield on account of the improvement obtained during the use of the process according to the invention, and also in terms of reduction in the amounts of active materials spread.

PROCESS EXAMPLE E

This process example gives an illustration of a process according to the invention which is useful for insecticidal treatment against *Nilaparvata lugens*.

The operating and measuring conditions are reproduced and adapted from Process Example B.

The active materials used, their application rates and the results obtained are collated in Table 5.

TABLE 5

|  | Plot No. 1 | Plot No. 2 | Plot No. 3 |
|---|---|---|---|
| Active material used in the process carried out | fipronil | deltamethrin | fipronil and deltamethrin |
| Rate of application of active material in the process | 25 g/ha | 6 g/ha | 8 g/ha of which 5 g/ha of fipronil and 3 g/ha of deltamethrin |
| Degree of variation in the number of damaging insects 3 days after application | +33% | +27% | −40% |
| Degree of variation in the number of damaging insects 7 days after application | +11% | 0% | −20% |

The results obtained during the use of this process according to the invention are thus particularly satisfactory, both in terms of insecticidal efficacy and in terms of reduction in the amounts of active materials spread.

Specifically, only the treatment process according to the invention using fipronil and deltamethrin as compounds (A) and (B) makes it possible to achieve a reduction in the number of damaging insects.

PROCESS EXAMPLE F

This process example gives an illustration of a process according to the invention which is useful for insecticidal treatment against *Nilaparvata lugens*.

The operating and measuring conditions are reproduced and adapted from Process Example B.

The active materials used, their application rates and the results obtained are collated in Table 6.

TABLE 6

|  | Plot No. 1 | Plot No. 2 | Plot No. 3 |
|---|---|---|---|
| Active material used in the process carried out | fipronil | cypermethrin | fipronil and cypermethrin |
| Rate of application of active material in the process | 25 g/ha | 12.5 g/ha | 17.5 g/ha of which 5 g/ha of fipronil and 12.5 g/ha of cypermethrin |
| Degree of variation in the number of damaging insects 3 days after application | +33% | −27% | −41% |
| Degree of variation in the number of damaging insects 7 days after application | +11% | +13% | −47% |

The results obtained during the use of this process according to the invention are thus particularly satisfactory, both in terms of insecticidal efficacy and in terms of reduction in the amounts of active materials spread.

Specifically, only the treatment process according to the invention using fipronil and cypermethrin as compounds (A) and (B) makes it possible to achieve a reduction in the number of damaging insects.

PROCESS EXAMPLE G

This process example gives an illustration of a process according to the invention which is useful for insecticidal treatment against *Nephotettix apicalis*. The operating and measuring conditions are reproduced and adapted from Process Example B.

The active materials used, their application rates and the results obtained are collated in Table 7.

TABLE 7

|  | Plot No. 1 | Plot No. 2 | Plot No. 3 | Plot No. 4 |
|---|---|---|---|---|
| Active material used in the process carried out | fipronil | deltamethrin | fipronil and deltamethrin | No treatment |
| Rate of application of active material in the process | 25 g/ha | 6 g/ha | 8 g/ha of which 5 g/ha of fipronil and 3 g/ha of deltamethrin | / |
| Degree of variation in the number of damaging insects 1 day after application | +50% | −13% | −53% | +200% |
| Degree of variation in the number of damaging insects 3 days after application | +83% | +25% | −32% | +200% |

TABLE 7-continued

|  | Plot No. 1 | Plot No. 2 | Plot No. 3 | Plot No. 4 |
|---|---|---|---|---|
| Degree of variation in the number of damaging insects 7 days after application | +183% | +75% | +11% | +522% |

The results obtained during the use of this process according to the invention are thus particularly satisfactory, both in terms of insecticidal efficacy and in terms of reduction in the amounts of active materials spread.

PROCESS EXAMPLE H

This process example gives an illustration of a process according to the invention which is useful for insecticidal treatment against *Nilaparvata lugens*.

The operating and measuring conditions are reproduced and adapted from Process Example B.

The active materials used, their application rates and the results obtained are collated in Table 8.

TABLE 8

|  | Plot No. 1 | Plot No. 2 | Plot No. 3 |
|---|---|---|---|
| Active material used in the process carried out | fipronil | fipronil and cypermethrin | No treatment |
| Rate of application of active material in the process | 25 g/ha | 25 g/ha of which 5 g/ha of fipronil and 20 g/ha of cypermethrin | / |
| Degree of variation in the number of damaging insects 1 day after application | −15% | −49% | +65% |
| Degree of variation in the number of damaging insects 3 days after application | −8% | −23% | +34% |
| Degree of variation in the number of damaging insects 7 days after application | −16% | −28% | +42% |
| Degree of variation in the number of damaging insects 14 days after application | +40% | +26% | +108% |

The results obtained during the use of this process according to the invention are thus particularly satisfactory, both in terms of insecticidal efficacy and in terms of reduction in the amounts of active materials spread.

PROCESS EXAMPLE I

This process example gives an illustration of a process according to the invention which is useful for insecticidal treatment against *Nilaparvata lugens*.

The operating and measuring conditions are reproduced and adapted from Process Example B.

The active materials used, their application rates and the results obtained are collated in Table 9.

TABLE 9

|  | Plot No. 1 | Plot No. 2 | Plot No. 3 |
|---|---|---|---|
| Active material used in the process carried out | fipronil | fipronil and cypermethrin | No treatment |
| Rate of application of active material in the process | 25 g/ha | 25 g/ha of which 5 g/ha of fipronil and 20 g/ha of cypermethrin | / |
| Degree of variation in the number of damaging insects 7 days after application | +19% | −14% | +113% |

The results obtained during the use of this process according to the invention are thus particularly satisfactory, both in terms of insecticidal efficacy and in terms of reduction in the amounts of active materials spread.

PROCESS EXAMPLE J

This process example proposes to give an illustration of an insecticidal treatment process according to the invention.

The treatment process used was a process of treatment against yellow rice stem borer or *Tryporyza incertulas* during the infestation of a rice crop.

The operating and measuring conditions are reproduced and adapted from Process Example B.

The active materials used, their application rates and the results obtained are collated in Table 10.

TABLE 10

|  | Plot No. 1 | Plot No. 2 | Plot No. 3 |
|---|---|---|---|
| Active material used in the process carried out | No treatment | fipronil | fipronil and cypermethrin |
| Rate of application of active material in the process | / | 25 g/ha | 25 g/ha of which 5 g/ha of fipronil and 20 g/ha of cypermethrin |
| Degree of variation in the number of dead plant cores | −26% | −35% | −66% |

The measurement was carried out by counting the number of rice plant cores that were dead due to attack by the damaging insects treated, i.e. *Tryporyza incertulas*; thus, the greatest degree of reduction is obtained after carrying out the process according to the invention, whereas the untreated plots or plots treated in a known manner give substantially more mediocre degrees.

These results thus show that the process according to the invention is of superior insecticidal efficacy while at the same time allowing a substantial reduction in the amounts of active materials spread and, concomitantly, a reduction in the environmental impact.

PROCESS EXAMPLE K

This process example proposes to give an illustration of an insecticidal treatment process according to the invention.

The treatment process used was a process of treatment against *Scotinophara lurida* during the infestation of a rice crop.

The operating and measuring conditions are reproduced and adapted from Process Example B.

The active materials used, their application rates and the results obtained are collated in Table 11.

TABLE 11

|  | Plot No. 1 | Plot No. 2 | Plot No. 3 |
|---|---|---|---|
| Active material used in the process carried out | No treatment | fipronil | fipronil and cypermethrin |
| Rate of application of active material in the process | / | 25 g/ha | 25 g/ha of which 5 g/ha of fipronil and 20 g/ha of cypermethrin |
| Degree of variation in the number of damaging insects 1 day after treatment | −21% | −43% | −52% |
| Degree of variation in the number of damaging insects 3 days after treatment | −40% | −67% | −81% |
| Degree of variation in the number of damaging insects 14 days after treatment | −27% | −45% | −60% |

These results thus show that the process according to the invention is of higher insecticidal efficacy while at the same time allowing a substantial reduction in the amounts of active materials spread and, concomitantly, a reduction in the environmental impact.

PROCESS EXAMPLE L

Maize seeds (variety Lorenzo) in a container under agitation were treated with the active ingredients, alone and in combination. Three treated seeds were sown in a 10-cm diameter pot. A week after sowing, each pot was infected with 10 L2 larvae of *Agrotis segetum* (turnip moth). The efficacy of the active ingredients at preventing feeding damage was determined 42 days after sowing. The test was carried out in a glasshouse at 22–27° C. and 30–70% relative humidity.

To indicate the existence of synergism between the active components the results were treated in the manner described by Colby S. R., "Calculating Synergistic and Antagonistic Responses of Herbicide Combinations" in Weeds 1967 15, 20–22. In this method the "expected" percent control of damage, E, of the combination compared with untreated control is given by the equation $$E = D + F - DF/100$$

where D is the % control by deltamethrin used alone at a given concentration and F is the % control by fipronil, used alone at a given concentration. If the observed control of the mixture is greater than E the results indicate synergism. The results are shown in the following table.

TABLE 12

| Table (Average of 3 treatments) | | | |
|---|---|---|---|
| Active ingredient (formulation) | Rate (g a.i./kg seed) | Control (% efficacy) | Expected (E) (%) |
| Untreated | — | 0 | |
| fipronil (FS 500 g/l) | 2, 5 | 50 | |
| deltamethrin (SC 50 g/l) | 0, 5 | 40 | |
| fipronil (FS 500 g/l) + deltamethrin (SC 50 g/l) | 2, 5 + 0, 5 | 90 | 70 |

In a particularly satisfactory manner, the results obtained in the various processes according to the invention carried out in Process Examples A to L required only a single application of the active materials (A) and (B) used, whereas, in the known usual practise, it is common to make use of several applications in order to achieve an acceptable or equivalent result.

Composition Examples A to G illustrate specific insecticidal compositions according to the invention.

COMPOSITION EXAMPLE A

According to a composition example according to the invention in the form of granules, the following constituents are used:

| | |
|---|---|
| 22.7 g of fipronil as insecticidal compound (A) and 27.3 g of deltamethrin as insecticidal compound (B) | 50 g |
| epichlorohydrin | 2.5 g |
| cetyl polyglycol ether | 2.5 g |
| polyethylene glycol | 35 g |
| kaolin with a particle size of between 0.3 and 0.8 mm | 910 g |

In this particular case, the insecticidal active materials are mixed with the epichlorohydrin and 60 g of acetone are added, followed by addition of the polyethylene glycol and the cetyl polyglycol ether. The kaolin is sprinkled with the solution obtained and the acetone is then evaporated off under vacuum.

COMPOSITION EXAMPLE B

According to a composition example according to the invention in the form of granules, the following constituents are used:

| | |
|---|---|
| 14.3 g of fipronil as insecticidal compound (A) and 35.7 g of cypermethrin as insecticidal compound (B) | 50 g |
| epichlorohydrin | 2.5 g |
| cetyl polyglycol ether | 2.5 g |
| polyethylene glycol | 35 g |
| kaolin with a particle size of between 0.3 and 0.8 mm | 910 g |

The process is then performed as described for Composition Example A.

COMPOSITION EXAMPLE C

This example proposes to illustrate a composition according to the invention, which is in the form of an emulsifiable concentrate.

| | |
|---|---|
| 7.2 g of fipronil as insecticidal compound (A) and 17.8 g of cypermethrin as insecticidal compound (B) | 25 g |
| tristyrylphenol/ethylene oxide condensate | 10 g |
| solution containing 70% by weight/volume of calcium dodecylbenzenesulphonate | 5 g |
| N-methylpyrrolidone | 50 g |
| light $C_{10}$ aromatic solvent | 10 g |

The first three components are dissolved in the N-methylpyrrolidone; the light $C_{10}$ aromatic solvent is then added to adjust to the final volume.

COMPOSITION EXAMPLE D

Another specific insecticidal composition according to the invention, which is in the form of an emulsifiable concentrate, is prepared using the following components:

| | |
|---|---|
| 15.6 g of fipronil as insecticidal compound (A) and 9.4 g of deltamethrin as insecticidal compound (B) | 25 g |
| tristyrylphenol/ethylene oxide condensate | 10 g |
| solution containing 70% by weight/volume of calcium dodecylbenzenesulphonate | 5 g |
| N-methylpyrrolidone | 50 g |
| light $C_{10}$ aromatic solvent | 10 g |

The process is then performed as described for Composition Example C.

COMPOSITION EXAMPLE E

According to a composition example according to the invention in the form of granules, the following constituents are used:

| | |
|---|---|
| 10 g of fipronil as insecticidal compound (A) and 40 g of cypermethrin as insecticidal compound (B) | 50 g |
| epichlorohydrin | 2.5 g |
| cetyl polyglycol ether | 2.5 g |
| polyethylene glycol | 35 g |
| kaolin with a particle size of between 0.3 and 0.8 mm | 910 g |

The process is then performed as described for Composition Example A.

COMPOSITION EXAMPLE F

According to another specific composition example according to the invention in the form of water-dispersible granules, the following constituents are used:

| | |
|---|---|
| 81.9 g of fipronil as insecticidal compound (A) and 98.1 g of deltamethrin as insecticidal compound (B) | 180 g |
| sodium lignosulphonate | 27 g |
| alkylnaphthalenesulphonates condensate | 18 g |
| alkylnaphthalenesulphonates | 4.5 g |

The ingredients are mixed together, micronized in a fluid-energy mill and then granulated in a rotary granulator by spraying with water (up to 10%). The granules thus obtained are dried in a fluidized-bed dryer in order to remove the excess water.

COMPOSITION EXAMPLE G

According to another specific composition example according to the invention in the form of water-dispersible granules, the following constituents are used:

| | |
|---|---|
| 36 g of fipronil as insecticidal compound (A) and 144 g of cypermethrin as insecticidal compound (B) | 180 g |
| sodium lignosulphonate | 27 g |
| alkylnaphthalenesulphonates condensate | 18 g |
| alkylnaphthalenesulphonates | 4.5 g |

The process is then performed as described for Composition Example F.

The Compositions Examples A to G, and also the Process Examples A to L, which have just been given clearly illustrate the superiority of the compositions and processes according to the invention over the known insecticides (A) and (B) alone.

The combination of the said process examples also allows a perfect illustration of the advantages provided by the treatment processes according to the invention, by means of compositions according to the invention comprising an insecticidal compound (A) and an insecticidal compound (B).

Satisfactory results are also obtained when insecticidal compositions according to the invention in the form of one or other of the insecticidal compositions according to the invention, in particular those illustrated by Composition Examples A to G, are used for the treatment processes according to the invention.

Moreover, no phytotoxicity phenomenon is observed in these process examples during treatments using the various insecticidal compositions according to the invention.

What is claimed is:

1. A process for killing rice-damaging arthropods in rice plants, comprising applying to said rice plants or to the soil in which they grow, a synergistically arthropodicidally effective amount of a combination of the insecticidal compound fipronil, which is 5-amino-3-cyano-1-(2,6-dichloro-4-trifluoromethylphenyl)-4-trifluoromethylsulfinylpyrazole, as compound (A), and an insecticidal compound (B) which is deltamethrin or cypermethrin, wherein the A/B weight ratio is between 0.1 and 5 when compound (B) is deltamethrin and between 0.05 and 10 when compound (B) is cypermethrin, and wherein from 0.5 to 500 g/ha of compound (A) and from 0.5 to 1000 g/ha of compound (B) are applied.

2. A process according to claim 1, wherein from 2 to 100 g/ha of compound (A) and from 1 to 500 g/ha of compound (B) are applied.

3. A process according to claim 1, wherein the A/B weight ratio is between 0.5 and 3 when compound (B) is deltamethrin, and between 0.15 and 6 when compound (B) is cypermethrin.

4. A process according to claim 2, wherein the A/B weight ratio is between 0.5 and 3 when compound (B) is deltamethrin, and between 0.15 and 6 when compound (B) is cypermethrin.

5. A process according to claim 1, wherein the arthropods are selected from the group consisting of *Tryporyza incertulas, Nephotettix apicalis, Nilaparvata lugens* and *Scotinophara lurida*.

6. A process according to claim 2, wherein the arthropods are selected from the group consisting of *Tryporyza incertulas, Nephotettix apicalis, Nilaparvata lugens* and *Scotinophara lurida*.

7. A process according to claim 3, wherein the arthropods are selected from the group consisting of *Tryporyza incertulas, Nephotettix apicalis, Nilaparvata lugens* and *Scotinophara lurida*.

8. A process according to claim 4, wherein the arthropods are selected from the group consisting of *Tryporyza incertulas, Nephotettix apicalis, Nilaparvata lugens* and *Scotinophara lurida*.

9. A process according to claim 3, wherein compound (B) is cypermethrin and wherein the A/B weight ratio is between 0.25 and 0.9.

10. A process according to claim 4, wherein compound (B) is cypermethrin and the A/B weight ratio is between 0.25 and 0.9.

11. A process according to claim 5, wherein compound (B) is cypermethrin and wherein the A/B weight ratio is between 0.25 and 0.9.

* * * * *